(12) United States Patent
Sauer et al.

(10) Patent No.: US 6,821,757 B2
(45) Date of Patent: Nov. 23, 2004

(54) RAPID AND SIMPLE PROCESS FOR ISOLATION OF CIRCULAR NUCLEIC ACIDS

(75) Inventors: Philippe Sauer, Hilden (DE); Jie Kang, Mettman (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 09/341,119

(22) PCT Filed: May 27, 1999

(86) PCT No.: PCT/EP99/03660

§ 371 (c)(1),
(2), (4) Date: Nov. 18, 1999

(87) PCT Pub. No.: WO99/61603

PCT Pub. Date: Dec. 2, 1999

(65) Prior Publication Data

US 2003/0032147 A1 Feb. 13, 2003

(30) Foreign Application Priority Data

May 27, 1998 (EP) .............................. 98109593

(51) Int. Cl.⁷ .......................... C12P 19/34; C07H 21/00
(52) U.S. Cl. .................... 435/91.1; 536/25.3; 536/25.4; 536/25.41
(58) Field of Search ....................... 435/91.1; 536/25.3, 536/25.4, 25.41

(56) References Cited

U.S. PATENT DOCUMENTS

| | | | | |
|---|---|---|---|---|
| 5,075,430 A | * | 12/1991 | Little | .......................... 536/27 |
| 5,234,809 A | * | 8/1993 | Boom et al. | .................... 435/91 |
| 6,027,750 A | * | 2/2000 | Gautsch et al. | .............. 424/489 |
| 6,027,945 A | * | 2/2000 | Smith et al. | ................. 436/526 |
| 6,180,778 B1 | * | 1/2001 | Bastian et al. | .............. 536/25.4 |

FOREIGN PATENT DOCUMENTS

| | | | |
|---|---|---|---|
| WO | WO95/01359 | | 1/1995 |
| WO | WO 95/21849 | * | 8/1995 |
| WO | WO97/29190 | | 8/1997 |

OTHER PUBLICATIONS

Segel, *Biochemical Calculations*, pp. 403, John Wiley & Sons, New York, 1976.*

Marko et al., "A Procedure for the Large-Scale Isolation of Highly Purified Plasmid DNA Using Alkaline Extraction and Binding to Glass Powder," *Analytical Biochemistry*, 121(2):382–387(1982).

Carter et al., "An inexpensive and simple method for DNA purifications on silica particles," *Nucleic Acids Research*, 21(4):1044 (1993).

* cited by examiner

Primary Examiner—Francisco Prats
(74) Attorney, Agent, or Firm—Jacobson Holman PLLC

(57) ABSTRACT

A method for separating and/or isolating circular nucleic acids from a mixture having different species of nucleic acids other than circular nucleic acids wherein the mixture is treated under alkaline conditions at a pH>8 with a solid matrix consisting essentially of a silica material in presence of at least one chaotropic substance.

18 Claims, No Drawings

RAPID AND SIMPLE PROCESS FOR ISOLATION OF CIRCULAR NUCLEIC ACIDS

The invention is concerned with a method for separating circular nucleic acids from a mixture having different species of nucleic acids. Furthermore, an aqueous buffer for the method is disclosed.

Many techniques in molecular biology require pure nucleic acids in general and plasmid DNA in particular.

Plasmids are double stranded circular closed DNA molecules which are found in certain organism additional to chromosomal DNA. Examples for such organism are some yeast and plant cells and all species of bacteria. While chromosomal DNA comprises all the information necessary for the cells to live, natural occurring plasmids are an additional genetic element providing and advantage to the host cell under certain environmental conditions.

Plasmids are a preferred tool in molecular biology due to the fact that they replicate autonomously from the chromosomal DNA and that they—in other than chromosomal DNA—can be isolated from bacteria cells in intact form. They can be hydrolysed at specific recognition sequences with commercially available restriction endonucleases, joined with fragment of foreign DNA, amplified with DNA polymerases and transferred into suitable cells.

The isolation of plasmid DNA is therefore often a prerequisite for subsequent molecular biological experiments, such as PCR reactions, sequencing reactions, cloning reactions, restriction hydrolyses, transformations and transfections.

Several methods for the isolation of plasmid DNA from bacterial cells are known. Common to all these methods is that they follow the scheme:
1. Formation of cleared lysate and
2. purification of plasmid DNA from the cleared lysate.

The steps for the formation of cleared lysate are almost identical between the different methods, characteristic differences only occur during the purification of plasmid DNA from the cleared lysate.

The formation of cleared lysate comprises the steps of:
cell lysis
precipitation of cellular components and subsequent
removal of the precipitate from the plasmid containing solution to form cleared lysate.

Cell lysis is usually realized under alkaline conditions in the presence of sodium dodecylsulfate resulting in bacterial crude lysate. To precipitate cellular components like chromosomal DNA, proteins, cellular debris etc., a potassium or sodium acetate buffer is added to the crude lysate, which adjusts the mixture to slightly acidic pH (4.8 to 5.0). Plasmid DNA does not precipitate under these conditions, so that it remains in the supernatant. In order to form a cleared lysate, the precipitate is removed from the plasmid containing solution either by centrifugation (Sambrook J., Fritsch E. F. and Maniatis T, (1989), "Molecular Cloning. A Laboratory Manual", pp. 7.49 to 7.50, Cold Spring Harbor Laboratory Press, Cold Spring Harbor, N.Y. Maniatis, Laboratory Manual), filtration (EP 0 616 638 B1) or magnetic separation using magnetically attractable beads which do not specifically bind the precipitate (U.S. Pat. No. 5,681,946 and U.S. Pat. No. 5,523,231). M. A. Marko et al. discloses in "Analytical Biochemistry", Vol. 121, No. 2, Apr. 19, 1982, pp. 382–387, a preparative procedure for obtaining highly purified plasmid DNA from bacterial cells. The method is adapted from an earlier procedure which gave partially purified plasmid in a form suitable for rapid screening of a large number of samples. In the method described all detectable RNA, chromosomal DNA and protein are removed without the use of enzymes phenol extraction dialysis or equilibrium centrifugation. Binding of plasmid DNA to glass powder in the presence of 6 M sodium perchlorate is used for the final purification step.

WO 95/01359 discloses a chromatographic purification and separation process for mixtures of nucleic acids. The nucleic acids to be separated and purified are adsorbed on a substrate from a solution which has a high salt concentration (ionic strength) and/or a high alcohol concentration, then desorption of the substrate is carried out by means of a solution with low salt concentration (ionic strength). The process in characterized in that the mixture of nucleic acids is adsorbed on a porous or non-porous mineral substrate made of metal oxides and/or mixed metal oxides, silica gel, materials composed mainly of glass, aluminium oxide, zeolithes, titanium dioxide, zirconium dioxide. The mixture of nucleic acids is adsorbed on the substrate from an aqueous adsorption solution with a high salt concentration (ionic strength) and with 1 to 50% by volume aliphatic alcohol with a 1 to 5 carbon atoms long chain, and/or polyethylene glycols (PEG) and/or hydrophobic, inorganic and/or organic polymers and/or organic acids, such as trichloracetic acid (TCA). If required, the mixture of nucleic acids is then washed with a washing solution, eluted with a solution having a lower salt concentration (ionic strength) and the thus obtained nucleic acid or nucleic acid fraction is collected. Carter, M. J., and Milton, I. D., disclose in "Nucleic Acids Research, 1993, Vol. 21, No. 4, Jan. 11, 1993 an inexpensive and simple method for "DNA purifications on silica particles. The method is a dissolving process concerning an already highly purified nucleic acid fraction which is bound to a matrix under non alkaline conditions.

WO-A 97/29190 discloses a scalable method for the production of highly purified plasmid DNA in *E. coli*. The method includes growing plasmid-containing cells to a high biomass in exponential growth and lysing the cells by raising the pH of the culture to a carefully controlled pH value in which chromosomal DNA is denatured but plasmid DNA is reversibly renatured. The method has been developed for the production of pharmaceutical grade DNA for use in in vivo and ex vivo gene therapy.

The methods for the purification of plasmid DNA from cleared lysate can be summarized —according to their underlying principle—into different groups.

One of these make use of density gradient centrifugation. This technique separates the components of the cleared lysate, like residual genomic DNA, RNA, proteins etc., according to their size in a caesium chloride gradient. The fraction, containing the plasmid DNA, is sucked off the centrifugational tube, further purified from salts by dialysis and finally concentrated by ethanol precipitation.

Methods of another group are based on the principle liquid-liquid extraction. The cleared lysate is several time extracted with phenol or a mixture of phenol and chloroform or a mixture of phenol, chloroform and an alcohol. During these extraction steps proteins, chromosomal DNA and other residual cellular impurities are transferred into the organic phase, while leaving the plasmid DNA in the aqueous phase. Traces from phenol were extracted several times with chloroform or a mixture of chloroform and an alcohol. The DNA is finally purified and concentrated by ethanol precipitation.

Other methods are based on anion exchange chromatography. The cleared lysate is applied on anion-exchange resin under appropriate salt and pH conditions. The binding conditions are thus adjusted that plasmid DNA are bound to the anion-exchange material but not impurities like RNA, Proteins, residual genomic DNA. After washing out impurities under salt conditions adjusting medium ionic strength, pure plasmid DNA is eluted under high ionic strength salt conditions. To remove the salt and to concentrate the plasmid DNA a final ethanol precipitation is necessary.

Purification of plasmid DNA using silica material is another basic principle. It uses the fact that DNA adsorb to silica material in the presence of chaotropic substances. The cleared lysate is mixed with a chaotropic buffer and subsequently applied to silica material, either a silica membrane or loose silica particles. After removal of the salts by a washing step DNA is eluted with a low salt buffer or water.

All known methods for the isolation of plasmid DNA from bacteria comprise the formation of cleared lysate. All known methods for clearing the bacterial lysate after precipitation of cellular particles, centrifugation, filtration and magnetic separation using magnetically attractable beads which do not specifically bind the precipitate, display considerable disadvantages. The lysate clearing by centrifugation is usually the most time consuming step in the corresponding plasmid isolation protocols. Lysate clearing by filtration, however, requires the application of an appropriate filter, which is commonly a major cost factor of the corresponding protocol.

It is an object of this invention to provide a process for the isolation of circular nucleic acids, in particular plasmid DNA directly from sources containing such nucleic acids among other. In particular, the nucleic acids are isolated from bacterial crude lysate avoiding the need to form cleared lysate.

According to the invention a method of separating circular nucleic acids from a mixture having different species of nucleic acids other than circular nucleic acids is disclosed which avoids the drawbacks of prior art.

According to the invention, the mixture containing circular nucleic acids is treated under alkaline conditions at a pH>8 with a solid matrix consisting essentially of a silica material in presence of at least one chaotropic substance. In particular the alkaline pH can be at least 9 or about 10. The upper pH value is limited by the individual circular nucleic acid. It depends on various conditions for example on the amount and the kind of chaotropic salt present. It is in the normal skill of an artisan how to optimize the respective separation conditions in view of the technical teaching of the present invention.

Preferably, the circular nucleic acid is double stranded DNA, particularly a plasmid.

In a preferred embodiment of the present invention, the method also renders possible the separation of circular nucleic acids when the mixture contains non circular nucleic acids and at least one other species of nucleic acids, such as RNA, single stranded DNA, double stranded linear DNA or circular open double stranded DNA or even combinations thereof. In many cases, a mixture of biological origin contains the above mentioned nucleic acids. They are often present in bacterial crude lysate.

Preferably, the chaotropic substance to be used is a chaotropic salt, such as a thiocyanate salt, urea, guanidinium salt, perchlorate salt, halogenid salt. Preferred are alkali salts of the respective chaotropic anion. Also alcohols, such as methanol, ethanol, n-propanol, isopropanol n-butanol, n-pentanol or combinations can be employed as chaotropic substances according to the invention.

Preferably, the silica material is a silica or glassfiber membrane, glass or silica in particulate form such as powder, beads or frits. It may be advantageous to use a silica material which is magnetic attractable, for example magnetic attractable beads with a silicaceous surface such as silica or glassfiber surfaces.

The alkaline conditions are adjusted by adding an aqueous solution of any suitable alkaline reacting substances, preferably an amphoteric substance such as an omega amino acid to the mixture containing circular nucleic acids to be separated and/or isolated. It is preferred to use an amphoteric substance having a weak acid and strong basic moiety such as $\omega$-amino acids. It is then possible to adjust the pH in the mixture from 8 to 12, more preferred 9 to 11, in particular about 10.

The invention is also related with an aqueous buffer comprising 6 to 9 M, preferably 7 to 8,5 M sodium thiocyanate, 0 to 20 Vol.-%, preferably 0 to 15 Vol.-% or more preferred 5 to 15 Vol.-% of $C_1$–$C_4$ alcohols such as ethanol or isopropanol, as well as buffer substances, in particular 25 to 130 mM amino acids, preferably $\omega$-amino acids such as glycine. Also basic amino acids such as lysine, arginine and histidine can be used.

In the following a preferred embodiment of the present invention is described in more detail.

The present invention related to a process for the separation and/or isolation of plasmid DNA from bacterial crude lysate, eliminating the need for preparing cleared lysate by precipitating cellular components and removing the precipitate by centrifugation or filtration.

More in particular, the present invention provide methods of plasmid purification from bacterial crude lysate comprising the use of novel buffer compositions to selectively bind plasmid DNA but not chromosomal DNA or other cellular impurities from the crude lysate to silica material. The selective binding of plasmid DNA to silica material in the presence of linear chromosomal DNA fragments and other cellular impurities is achieved by adjusting alkaline binding conditions in the presence of high concentrations of chaotropic substances.

The mixture to be separated according to the invention can be obtained by a method comprising the steps of:
  cell lysis
  adjustment of appropriate conditions for selective binding of plasmid DNA preventing binding of linear DNA to silica material.
  selective adsorption of plasmid DNA to a silica surface
  washing of the silica material
  elution of the plasmid DNA from the silica material.

Preferably, the method of the invention is employed for purification of plasmid DNA from bacterial crude lysate without precipitation of cellular components and lysate clearing. The term plasmid, as used in the present specifications, means circular closed DNA molecules, either single or double stranded, which are autosomal replicable in a bacterial cell; no matter whether it is a naturally occurring plasmid or a genetically engineered.

The invention comprises the steps of:
  1. lysis of bacterial cells
  2. adjusting binding conditions for selective binding of plasmid DNA in the presence of linear DNA and all other cellular components
  3. binding of plasmid DNA to silica material
  4. washing of the silica material
  5. elution of plasmid DNA.

In one embodiment of the invention the bacterial cell lysis is performed according to the traditional alkaline lysis. The bacterial cells are harvested and resuspended in low salt buffer, containing 50 mM Tris.Cl, 10 mM EDTA, pH 8.0 and 300 $\mu$g/ml RNase A. Other species of RNase, like RNase T2, may be used but RNase A is most suitable for commercial application since it is available for a low prices. Bacterial cells are lysed after addition of an alkaline buffer containing a strong detergent. The most efficient detergent in the respect is sodium dodecylsulfate, but other detergents like Tween 20, choleic acid, deoxycholic acid and CHAPS are—to a lower amount of magnitude—suitable to lyse bacterial cells under strongly alkaline conditions. Most efficient cell lysis for the purpose of plasmid isolation is effected in a mixture with final concentration of about 100 mM sodium hydroxide and about 0.5% of sodium dodecylsulfate.

Alternatively, plasmid DNA can be purified from the "crude lysate" which can be established by a proteinase K cell-digest, or by an ultra-sonic lysis. The method of the invention is not limited to lysis of cells performed according to alkaline lysis.

The immobilization of plasmid DNA in the process according to the invention is performed by selectively and specifically bind the plasmid DNA to silica material in the presence of at least one chaotropic substance. The term specifically binding of DNA to silica material, as used in the present specifications, means that the DNA is adsorbed to the silica material and not only unspecifically attached. The term silica material, as used in the present specifications, means crystals of silicium dioxide and/or other forms of silicon oxides, such as glass powder, zeolite, no matter whether the basic solid is a membrane, resin, loose particles or magnetic beads. The term chaotropic substance, as used in the present specifications, means every substance which is able to alter the secondary and/or tertiary and/or quaternary structure of a polymer without affecting the primary structure. Examples for chaotropic substances are isothiocyanate salts, sodium iodide, sodium perchlorate, guanidinium salts, urea and short chain alcohols. Chaotropic substances are known to alter the secondary structure of polymers in general and or nucleic acids in particular. This alteration can be measured in the decrease of the melting point of double stranded DNA. All kinds of nucleic acids, single stranded DNA, double stranded circular closed DNA, double stranded linear DNA and RNA can be immobilized on silica material under appropriated chaotropic conditions. The optimal chaotropic conditions, e.g. kind and concentration of the chaotropic substances, for the immobilization of nucleic acids to silica material vary among the different species of nucleic acids. Typical binding conditions of plasmid DNA are 2 to 4 M solutions of guanidinium hydrochloride or guanidinium thiocyanate, displaying a pH of 4 to 7. The particular optimum depends mainly on the viscosity of the mixture, the content of proteins and other substances. In general, however, under the conditions, when circular double stranded DNA is bound, linear double stranded DNA with a similar size is also bound.

Intriguingly, the chaotropic properties show some influence on the pH value which is adjusting when dissolving the chaotropic substance in water. When chaotropic substances which have a chaotropic potency are employed, a pH shift may occur. When the buffer conditions are selected for the isolation or separation of the nucleic acids according to the invention, it is advisable to check the pH adjustment when dissolving the chaotropic substance which will be employed during the operation.

Known methods for plasmid purification make use of immobilization of the plasmid DNA to silica material in the presence of chaotropic salts, the immobilization step is performed from bacterial cleared lysate. The term bacterial cleared lysate, as used in the present specifications means bacterial cell lysate, whereof cellular components are removed by precipitation and subsequent removal of the precipitate by centrifugation or filtration.

In the process for plasmid isolation according to a preferred embodiment of the invention plasmid binding to the silica material is performed starting from the crude lysate. The term bacterial crude lysate means lysed bacterial cells of which essentially no components are removed by a separation step in general respectively a precipitation step in particular. Under commonly adjusted chaotropic conditions for the binding of plasmid DNA to silica surface, present linear DNA fragments—such as sheared fragments of chromosomal DNA—are bound to the silica material additional to the plasmid DNA. Therefore, these methods require precipitation of genomic DNA and subsequent removal either by centrifugation or filtration to acquire a clean plasmid purification.

The process according to the invention renders possible to avoid the steps of precipitating cellular components, and removal of the precipitate by adjusting the chaotropic conditions in the binding mixture in a way, that substantially only plasmid DNA but not chromosomal DNA present in the mixture binds to the silica surface. This is achieved with high molar chaotropic mixtures comprising alkaline pH as binding buffer. It is known that within a certain range of pH (pH 12.0 to 12.5) plasmid DNA remains undenatured whereas chromosomal DNA is denatured (Birnboim H. C. & Doly J., (1979), "A rapid alkaline extraction procedure for screening recombinant plasmid DNA", Nucleic Acids Res 7(6), 1513 to 1523). If the pH is smaller than the lower boundary of this range, both plasmid DNA and linear chromosomal DNA fragments are undenaturated, if the pH is larger than the upper boundary of this pH range both kinds of DNA are denaturated. The process according to this invention takes advantage of the fact that this range of pH is shifted to lower pH values and broadened from 0.5 pH units up to more than 3 pH units in the presence of high molar chaotropic substances. The magnitude of this pH range and the absolute pH value depends on the species of chaotropic salt used and its concentration; in tendency, the higher the concentration of chaotropic salt and the stronger the chaotropic salt, the lower and broader is the pH range which causes denaturation of linear DNA but not of plasmid. Chaotropic substances in this respect are the chaotropic substances mentioned above.

Furthermore, the invention takes advantage of the effect that under the conditions—presence of high molar chaotropic substances at alkaline pH—circular closed double stranded DNA (e.g. plasmid) but not linear DNA fragments (e.g. sheared chromosomal DNA) specifically binds to silica material. The precise pH may be adjusted with all kinds of pH buffers effective in this range of pH. Examples are phosphate buffers, glycine buffers and boric acid/sodium hydroxide buffer. Due to its high buffer capacity in particular glycine buffers seem to be suitable for this purpose.

Another aspect of the process according to the invention is that it affects solubilization of all the cellular components present after alkaline bacterial cell lysis. This is partially affected by the presence of high concentrations of chaotropic substances which unfold most of the present polymers, such as polysaccharides, proteins, peptides etc. It is further affected by the presence of strong detergents. The most effective surfactant in this respect is sodium dodecylsulfate, which also plays an important part during the bacterial cell lysis. Due to the heterogenous character of the cellular components which have to be solubilized, addition of a second detergent is advisable. Suitable for these purposes are members of all classes of detergents except cationic surfactants. Thus, for example anionic surfactant like choleic acid and deoxycholic acid, non-ionic surfactants like Tween 20, zwitterionic surfactants like CHAPS function well.

Summarized, the binding buffer according to the inventions allows selective binding of plasmid DNA to silica material in the presence of all cellular components including linear DNA fragments:

1. by avoiding precipitation of cellular components
2. by denaturating proteins and chromosomal DNA but not plasmid DNA
3. by adjusting chaotropic conditions which allow binding of plasmid DNA but not of linear DNA fragments in general and of sheared chromosomal DNA in particular to silica material as well as
4. by solubilizing the cellular components to a homogenous mixture.

Immobilization of nucleic acid such as DNA is performed by adsorption of the nucleic acid to silica material in the presence of high salt; which is well known in the field of molecular biology for nearly 20 years (Vogelstein B. & Gillespie D., (1979), "Preparative and analytical purification of DNA from agarose", Proc. Natl. Acad. Sci. 76(2): 615 to 619).

Several kinds of silica material have been tested according to the present invention: magnetic silica particles, loose silica particles and silica membranes.

Washing of the silica material after the binding step is preferred. On the one hand, impurities arising from the biological sample, which are present at the silica material after the binding step, and on the other hand the chaotropic substances applied in the binding, which are partially attached to the silica material. Both should be removed from the silica material.

The removal of these impurities is not only recommendable in the process according to the present invention but in all known processes preferably for DNA purification using silica material.

Impurities arising from the biological sample after the binding step on the silica surface are mainly due to two reasons.

Substantially all silica materials provide a certain death volume, depending on the kind of silica material and the amount of silica material applied for e.g. DNA purification. Preferably, the death volume should not exceed about 50 $\mu$l. The death volume of silica material provided in commercially available kits for purification of up to 20 $\mu$g plasmid DNA from a 5 ml bacterial overnight culture lies in the range of 2 to 5 $\mu$l. Death volume in this context means the difference of the wet to the dry volume of the silica material. The death volume after each purification step consists of the buffer applied in this step. Thus, after the binding step, the death volume of the silica material consists of the binding mixture, containing all cellular components.

In the process according to the invention these impurities are substantially removed by the application of a washing buffer, containing high amounts of a chaotropic substance at alkaline pH. The chaotropic substance solubilizes the impurities and removes them from the silica membrane. The alkaline pH is prefered to prevent binding of the denatured chromosomal DNA to the silica material. The adjustment of the appropriate pH is accomplished with the pH-buffers mentioned for the binding buffer.

Basically, the washing buffer according to the process of this invention works in an analogous way as the binding buffer. Since e.g. DNA, specifically bound to silica material, display slightly different characteristics according to chaotropic buffers, the washing buffer must display a slightly different composition as the binding mixture. Preferably, the washing buffer comprises in particular short chain aliphatic alcohols such as isopropanol or ethanol in the range of 5 to 40 vol-%, preferably of 20 to 40 vol-% final concentration. Since short chain alcohols are itself chaotropic, it is tolerable that the concentration of chaotropic salts is slightly lower in the appropriate washing buffer than in the corresponding binding buffer. Typical concentration—depending of the kind of chaotropic salt used—are within the range of 4 to 9, preferably of 4 to 6 molar.

Alternatively, also neutral or moderate acidic washing buffers can be used. A neutral or acidic chaotropic buffer contains 1,5–3 M chaotropic salt in presence of 10–30% ethanol or isopropanol as for adjusting the pH up to about 4.

After washing out the impurities from the biological sample, the chaotropic salts have to be removed from the silica material. This is done with one or more washing steps with an alcohol or water solution. Typically ethanol (preferably about 80%) is used, but other short chain alcohols work as well.

Elution of plasmid DNA is performed either with pure water or with low salt buffers.

The process of the invention can easily be performed by the customer when the materials used in the process are provided in form of a kit. Therefore, also a kit is subject of the present invention which comprises an aqueous buffer comprising 6 to 9 M preferably 7–8,5 M sodium thiocyanate, 0 to 20 vol.-% 0 to 15 vol.-% or more preferred 5 to 15 Vol.-% of $C_1$–$C_4$ alcohols such as ethanol or isopropanol, 25 to 130 mM buffer substances in particular amino acids preferably $\omega$-amino acids such as glycine. The kit according to the invention may further contain auxiliary materials such as columns with or without silicaceous material, silicaceous material in suspension form, further buffers and instruction manuals. Further buffers are preferably those which are used in the process of the invention as, for example, resuspension buffer, lysis buffer, washing buffer, elution buffers and the like. Also spin columns may be incorporated in the respective kit. The configuration of such kit is in particular corresponding to the protocol to be followed by the customer.

Typical protocols are further explained in the following examples.

EXAMPLES

Buffer Compositions

Resuspension Buffer (P1): 50 mM Tris.Cl, 10 mM EDTA, pH 8.0;
    300 $\mu$g/ml RNase-A
Lysis Buffer (P2): 100 mM NaOH, 0.1% SDS
Binding-Buffer (PB): 7.6 M NaSCN, 10% EtOH (v/v), 5% Tween 20;
    60 mM glycine, pH 9.6 or 8.2 NaSCN, 10% ethanol (v/v), 5% Tween 20, 60 mM glycine, pH 9.6
Washing Buffer (PW1): 5.5 M NaSCN, 30% EtOH, 100 mM Glycine pH 9.6 or
    1.5 M GuHCl, 30% (v/v) Isopropanol, 150 Kaliumacetat, pH 5,1
Washing Buffer (PW2): 80% EtOH, 10 mM Tris.Cl, pH 7.5
Elution Buffer (PE): 10 mM Tris.Cl, pH 8.5

Silica Materials

Spin columns containing silica-gel membranes supplied by Qiagen GmbH, Hilden, Germany which may comprise stucks of several membrane layers.

Silica resin suspension: commercially available QIAEX II gel extraction kit supplied by Qiagen GmbH, Hilden, Germany Magnetic silica beads, AGOWAmag®, AGOWA, Germany.

Protocol A

This protocol is suitable for isolation of up to 10 µg of plasmid DNA from bacterial overnight cultures of up to 1.5 ml. The procedure uses spin columns containing silicagel membranes, and all steps are performed at maximum speed≧10,000×g or 13,000 rpm) in a conventional table-top microcentrifuge unless otherwise stated.

Advantageously, the process of the invention can be performed in multi well plates having 96 wells, 384 wells or even more wells. Due to this, the process of the invention may be employeds with automatic pipetting machines, e. g. the BioRobot® of Qiagen®, Hilden, Germany.

1. Harvest an appropriate volume of bacterial overnight-culture in a microcentrifuge at 5.000×g.
2. Resuspend pelleted bacterial cells in 100 µl of Buffer P1.
3. Add 100 µl of Buffer P2, mix the sample by vortexing, and incubate at room temperature for 5 min.
4. Add 500 µl of Buffer PB and mix thoroughly by vortexing vigorously.
5. Place a spin column in a microcentrifuge tube, and apply the sample to the spin column.
6. Centrifuge for 1 min and discard the flow-through.
7. To wash, add 500 µl of Buffer PW1 to the spin column, centrifuge for 1 min and discard the flow-through.
8. To wash, add 750 µl of Buffer PW2 to the spin column, centrifuge for 1 min and discard the flow-through.
9. Centrifuge for an additional 1 min to remove residual washing buffer.
10. Transfer the spin column into a clean microreaction tube. To elute DNA, add 50 µl of Buffer PE to the center of each spin column, let stand for 1 min, and centrifuge for 1 min.

Protocol B

This protocol is suitable for isolation of up to 10 µg plasmid DNA from bacterial overnight cultures of up to 1.5 ml. The procedure uses QIAEX II silica particles, and all steps are performed in microcentrifuge tubes. Centrifugation steps are carried out at maximum speed (≧10,000×g or 13,000 rpm) in a conventional table-top microcentrifuge unless otherwise stated.

1. Harvest an appropriate volume of bacterial overnight culture in a microcentrifuge at 5.000×g.
2. Resuspend pelleted bacterial cells in 100 µl of Buffer P1.
3. Add 100 µl of Buffer P2, mix the sample by vortexing and incubate at RT for 5 min.
4. Add 500 µl of Buffer PB.
5. Resuspended QIAEX II by vortexing for 30 sec. Add 25 µl of QIAEX II to the sample and mix thoroughly by vortexing vigorously.
6. Incubate at room temperature for 5 min, then centrifuge for 30 sec at>10,000×g and remove discard the supernatant with a pipet.
7. Wash the pellet with 750 µl of Buffer PW1, resuspending the pellet by vortexing, and centrifuging for 30 sec. Remove all traces of supernatant.
8. Wash the pellet twice with 750 µl of Buffer PW2, resuspending the sample for 30 sec. Remove all traces of supernatant.
9. Air-dry the pellet at room temperature for 20 min.
10. To elute, add 60 µl of Buffer PE and resuspend the pellet by vortexing, Incubate at room temperature for 5 min.
11. Centrifuge for 30 sec. Carefully pipet the supernatant into a clean tube.
12. Optional: repeat steps 10 and 11 and combine the eluates.

Protocol C

This protocol is suitable for parallel isolation of up to 10 µg plasmid DNA from 96 bacterial overnight cultures. The procedure uses magnetic silica particles, and all steps are performed in 96-well microtiter plate format. For steps requiring repeated pipetting, a reservoir or multichannel pipet can greatly facilitate liquid handling.

1. Harvest appropriate volumes of bacterial overnight culture at 5.000×g.
2. Resuspend the pelleted bacterial cells in 100 µl of Buffer P1 and transfer the samples to the well of a 96-well round-well block.
3. Add 100 µl of Buffer P2 to each well. Mix thoroughly by vortexing the block and incubate at room temperature for 5 min.
4. Mix 50 ml of Buffer PB and 2 ml of magnetic silica suspension in a plastic beaker. Add 520 µl of this suspension to each well of the round-well block.
5. Seal the block with adhesive tape and mix thoroughly by shaking the block vigorously. Incubate on a shaker at room temperature for 5 min.
6. Place the block into a magnetic separator, remove the tape, and let stand for 1 min. Discard the supernatants.
7. Remove the block from the magnetic separator. Add 750 µl of Buffer PW1 to each well. Seal the block with adhesive tape and mix thoroughly by shaking the block vigorously.
8. Place the block back into the magnetic separator, remove the tape, and let stand for 1 min. Discard the supernatants.
9. Remove the block from the magnetic separator. Add 750 µl of Buffer PW2 to each well. Seal the block with adhesive tape and mix thoroughly by shaking the block vigorously.
10. Place the block back into the magnetic separator, remove the tape, and let stand for 1 min. Discard the supernatants.
11. Repeat steps 9, 10, but discard only 600 µl of each supernatant.
12. Remove the block from the magnetic separator, and resuspend the magnetic particles in the residual supernatant by vortexing. Transfer the sample to the wells of a 96-well microtiter plate. Place the microtiter plate into the magnetic separator, let stand for 1 min and remove the residual supernatant.
13. Air-dry the microtiter plate at room temperature for 20 min.
14. To elute DNA, add 60 µl of Buffer PE to each well, resuspend the pellets, and incubate the microplate on a shaker for 5 min.
15. Place the microplate into the magnetic separator and let stand for 1 min. Transfer the supernatants into a clean 96-well microtiter plate.
16. Optional: repeat steps 14 and 15 and combine the eluates.

Example 1

Specific Binding of Circular Plasmid DNA to Silica Material in the Presence of Linear DNA This example demonstrates the property of the binding buffer according to this invention to selectively bind double stranded circular closed DNA to silica material in the presence of double stranded linear DNA.

500 ng of pUC19 plasmid DNA were spiked with total 1 µg of double stranded linear DNA fragments within a size range of 150 bp to 20 kb, which were produced by an enzymatic hydrolysis of lambda phage DNA with the restriction endonucleases Hind III and Eco RI. This DNA mixture was purified according to protocol A and protocol C with slight modifications. They were performed using the buffers describes above, with the modification of adding the DNA mixture to 100 µl of buffer P1 and omit the application of bacterial cells. Additionally, the purification according to each of the two protocols were performed with two modified binding buffers, one consisting of 4 M potassium thiocyanate, 30% isopropanol and 10 mN Tris.Cl adjusted to a pH of 7.0 (Buffer C2) and another consisting of 8.8 M sodium Thiocyanate, 10% EtOH, 10 mM Tris.Cl adjusted to a pH of 7.0 (Buffer C3).

The eluates contains pure plasmid DNA without traces of linear DNA if alkaline binding buffer is used. If modified binding buffers with neutral pH instead of alkaline pH is used, a mixture consisting of linear DNA fragment and plasmid DNA were obtained.

This experiment clearly shows that only the combination of a chaotropic salt and an alkaline pH in the binding mixture allows selective binding of the circular plasmid but not of linear DNA.

Example 2
Determination of pH Range Allowing Selective Binding of Plasmid DNA

This example determines the pH range where selective binding of plasmid DNA from a mixture of plasmid DNA and sheared genomic DNA fragment is possible. Genomic DNA was prepared from *Escherichia coli* using the silica membranes like membranes as QIAamp Tissue Kit (QIAGEN) (Molecular cloning (1)). 2 µg of genomic DNA were mixed with 2 µg of pUC19 plasmid DNA and purified according to protocol C (with the modification of adding the DNA mixture to 100 µl of buffer P1 and omit the application of bacterial cells) with a modified binding buffer. The binding buffer consist of 4 M potassium thiocyanate, 0,6 M sodium chloride, 0,1 M glycine and 30% ethanol adjusted so that the pH in the binding mixture is between 11.1 and 12.4.

At a pH value of 11.1 small traces of genomic DNA were copurified indicating the that separation between plasmid and genomic DNA is incomplete at his pH. Within a range of pH from 11.25 to 12.0 plasmid DNA is selectively purified free from impurities of genomic DNA. For a pH above 12.0 neither plasmid nor genomic DNA could be obtained.

The same experiment was performed with a more chaotropic binding buffer, consisting of 8.8 M sodium thiocyanate. In this case, complete separation of plasmid and genomic DNA could be achieved within a pH range of 9.2 to 11.1.

Example 3
Specific Removal of Linear DNA from Mixture of Linear DNA and Plasmid DNA Bound to Silica Material This example demonstrate that linear DNA, once bound to silica material, can be selectively washed away with a chaotropic buffer at alkaline pH. Two mixture consisting of 1 µg plasmid DNA and total 2 µg of double stranded linear DNA fragments within a size range of 150 bp to 20 kb, which were produced as described in example 1, were bound with a modified binding buffer—consisting of 4 M potassium isothiocyanate and 30% ethanol—to the silica membrane of two QIAamp spin column (QIAGEN) according to protocol A (steps 1 to 5, with the modification of adding the DNA mixture to 100 µl of buffer P1 and omit the application of bacterial cells). The modified binding buffer was known (see example 2) to bind both, plasmid and genomic DNA to silica membranes.

The residual steps of protocol A (steps 6 to 9) were performed by using the washing buffer W1 (5.5 M NaSCN, 30% EtOH, 100 mM glycine, pH 9.6) for one spin column and by using a modified washing buffer PWC (containing 5 M guanidine hydrochloride, 30% isopropanol and 10 mM tris.Cl adjusted to a pH of 7.0).

When the chaotropic washing buffer adjusted to an alkaline pH (washing buffer W1) was used, plasmid DNA pure rid from linear DNA could be obtained. However, when using a comparable chaotropic washing buffer which was adjusted to neutral pH (buffer PWC), a mixture of plasmid and linear DNA was purified.

This experiment show that a chaotropic buffer comprising alkaline pH is able to selectively remove linear DNA from a mixture of circular closed and linear DNA by not affecting the binding of circular closed DNA.

Example 4
Isolation of Plasmid DNA from *Escherichia coli* Using Silica Membranes This example describes the standard plasmid isolation procedure according to this invention using a silica membrane.

1.5 ml overnight cultures of several *Escherichia coli* strains containing plasmids were purified according to protocol A. Between 2 and 5 µg of pure plasmid DNA were obtained from each sample.

Example 5
Isolation of Plasmid DNA from *Escherichia coli* Using Loose Silica Resin This example describes the standard plasmid isolation procedures according to this invention using a loose silica particles.

1.5 ml overnight cultures of several *Escherichia coli* strains containing plasmids were purified according to protocol B. QIAEX II particles were used as silica particles. Between 2 and 5 µg of pure plasmid DNA were obtained from each sample.

Example 6
Isolation of Plasmid DNA from *Escherichia coli* Using Magnetic Silica Particles 1.5 ml overnight cultures of several *Escherichia coli* strains containing plasmids were purified according to protocol C. Magnetic beads from QIAGEN were in this experiment. Between 2 and 5 µg of pure plasmid DNA were obtained from each sample.

What is claimed is:

1. A method for separating and/or isolating circular nucleic acids from a bacterial crude lysate mixture wherein the mixture is treated under alkaline conditions at a pH of 8 to 12 with a solid matrix consisting essentially of a silica material in the presence of at least one chaotropic substance present at a concentration of 4–9 M.

2. The method of claim 1, wherein the circular nucleic acid is double stranded DNA.

3. The method of claim 1, wherein the mixture contains non circular nucleic acids and at least one other species of nucleic acids.

4. The method of claim 1, wherein the chaotropic substance is a chaotropic salt and/or the chaotropic substance is an alcohol.

5. The method of claim 1, wherein the silica material is a silica or glassier membrane, glass or silica in particulate form, beads or frits and/or silica-gel membranes comprising stacks of multi layer membranes.

6. The method of claim 1, wherein the silica material is magnetic attractable beads with a silicaceous surface.

7. The method of claim 1, wherein the alkaline conditions are adjusted by adding an aqueous solution of an amphoteric substance.

8. The method of claim 1, performed in multi well plates.

9. The method of claim 1, performed using automatic pipetting machines.

10. The method of claim 1, wherein the following process steps are performed:

cell lysis adjustment of conditions for selective binding of plasmid DNA preventing binding of linear DNA to silica material selective absorption of plasmid DNA to a silica surface washing of the silica material elution of the plasmid DNA from the silica material.

11. The method of claim 1, wherein the circular nucleic acid is a plasmid.

12. The method of claim 1, wherein the mixture contains non-circular nucleic acids and at least one other species of nucleic acids selected from the group consisting of RNA, single stranded DNA, double stranded linear DNA, circular open double stranded DNA, and combinations thereof.

13. The method of claim 1, wherein the chaotropic substance is a thiocyanate, urea, guanidinium salt, perchlorate salt, a halide salt and/or the chaotropic substance is methanol, ethanol, n-propanol, isopropanol, n-butanol, n-pentanol, or combinations or said chaotropic substances.

14. The method of claim 1, wherein the silica material is a silica or glassier membrane, glass or silica in powder form, beads or frits and/or silica-gel membranes comprising stacks of several membrane layers (multi layer membranes).

15. The method of claim 1, wherein the silica material is magnetic attractable beads with a silica or glass-fiber surface.

16. The method of claim 1, wherein the alkaline conditions are adjusted by adding an aqueous solution of an amphoteric omega amino acid.

17. The method of claim 1, wherein the alkaline conditions are adjusted by adding an aqueous solution of an amphoteric omega amino acid to effect a pH between 8 and 12 in the resulting mixture.

18. The method of claim 1, performed in multi well plates of 384 or 96 wells.

* * * * *